(12) United States Patent
Del Rio et al.

(10) Patent No.: US 6,733,218 B2
(45) Date of Patent: May 11, 2004

(54) HIGH SPEED SURGICAL INSTRUMENT

(75) Inventors: Eddy Del Rio, Royal Palm Beach, FL (US); Jose M. Lamanna, Jupiter, FL (US); Douglas A. Perry, Palm Beach Gardens, FL (US); Thomas E. Anspach, Jupiter, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 302 days.

(21) Appl. No.: 09/962,957

(22) Filed: Sep. 25, 2001

(65) Prior Publication Data

US 2003/0060841 A1 Mar. 27, 2003

(51) Int. Cl.⁷ .............................. B23C 1/00; A61B 17/00
(52) U.S. Cl. ..................... 409/231; 409/232; 606/80; 606/96; 408/226; 408/231; 408/232; 279/79; 279/84; 279/97
(58) Field of Search ............................. 409/231, 232; 279/79, 84, 97; 408/226, 231, 232; 606/80, 96; 192/72, 73, 77, 78, 69.61, 69.7, 70.15

(56) References Cited

U.S. PATENT DOCUMENTS

| | | | | |
|---|---|---|---|---|
| 1,376,139 A | * | 4/1921 | Porto ........................ 403/104 |
| 2,752,965 A | * | 7/1956 | Mackey ...................... 408/211 |
| 2,958,349 A | * | 11/1960 | McNutt ....................... 408/67 |
| 3,011,369 A | * | 12/1961 | Russell ........................ 408/80 |
| 3,865,502 A | * | 2/1975 | Hamann ..................... 408/226 |
| 3,907,452 A | * | 9/1975 | Tripp ........................... 408/56 |
| 4,076,444 A | * | 2/1978 | Siebrecht .................... 408/226 |
| 4,375,341 A | * | 3/1983 | Schulze .................... 408/72 R |
| 5,624,214 A | * | 4/1997 | Carroll ....................... 408/226 |
| 5,833,704 A | * | 11/1998 | McCombs et al. ............ 606/80 |
| 5,904,687 A | * | 5/1999 | Del Rio et al. ................ 606/80 |
| 6,171,033 B1 | * | 1/2001 | Wrobel ................... 408/239 R |
| 6,293,172 B1 | * | 9/2001 | Smith ........................ 81/57.13 |

* cited by examiner

Primary Examiner—A. L. Wellington
Assistant Examiner—Dana Ross
(74) Attorney, Agent, or Firm—Norman Friedland

(57) ABSTRACT

A high speed surgical instrument is designed with a clutch that automatically locks a cutter which is easily assembled and disassembled without moving parts. The clutch includes a pin and U-shaped pin that compliments a configured groove section at the proximal end of a cutter that fits into a clutch mechanism in the drill or attachment. The cutter includes axially spaced and opposed grooves judiciously located and a flat end portion that allows easy ingress and egress for locking into the clutch mechanism. A square or multi-sided bore configuration of a journal type bearing made from a high temperature resistance polymer material allows the drill to operate at high speeds with a reduction in the diameter of the distal end of the cutter support.

32 Claims, 7 Drawing Sheets

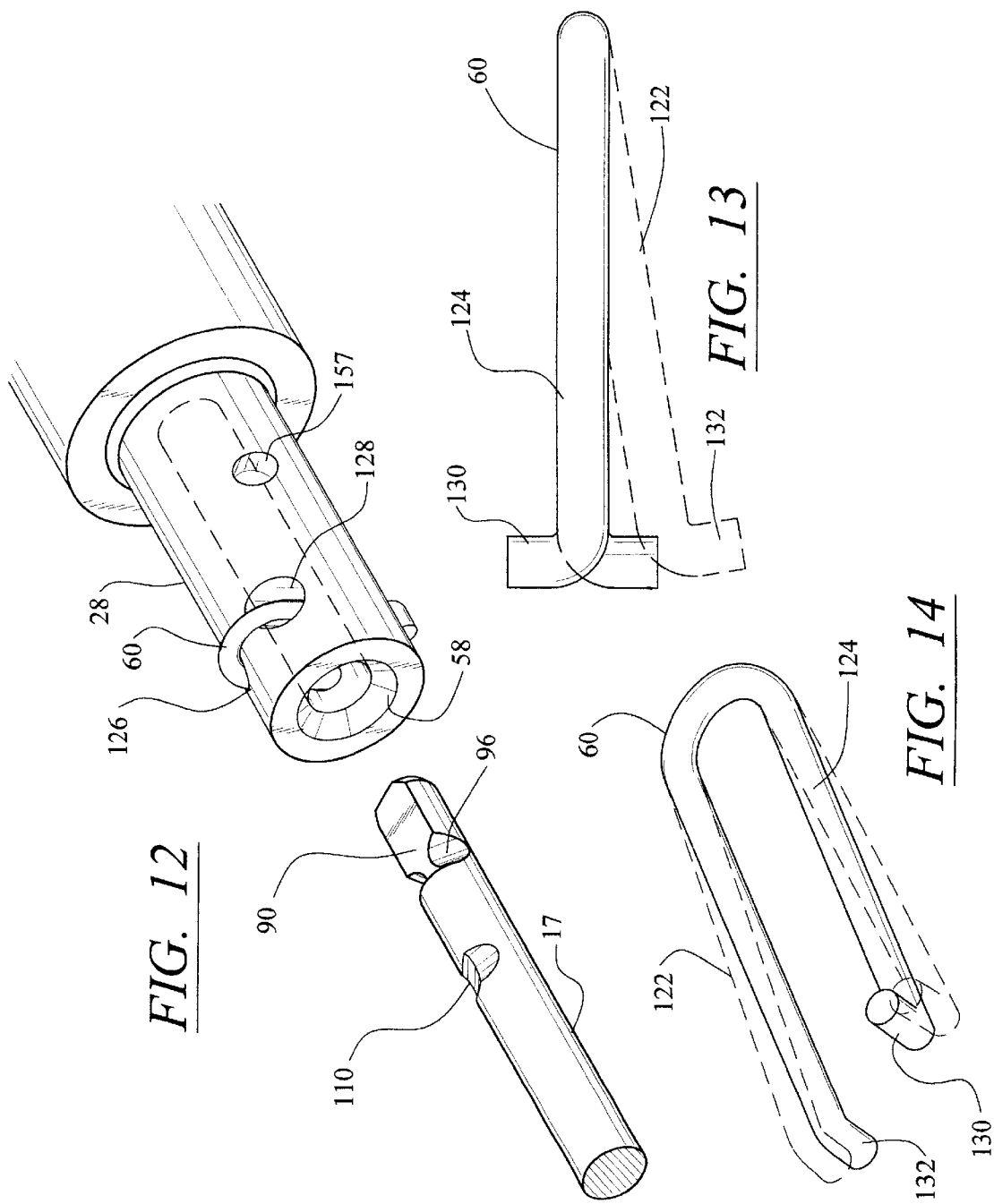

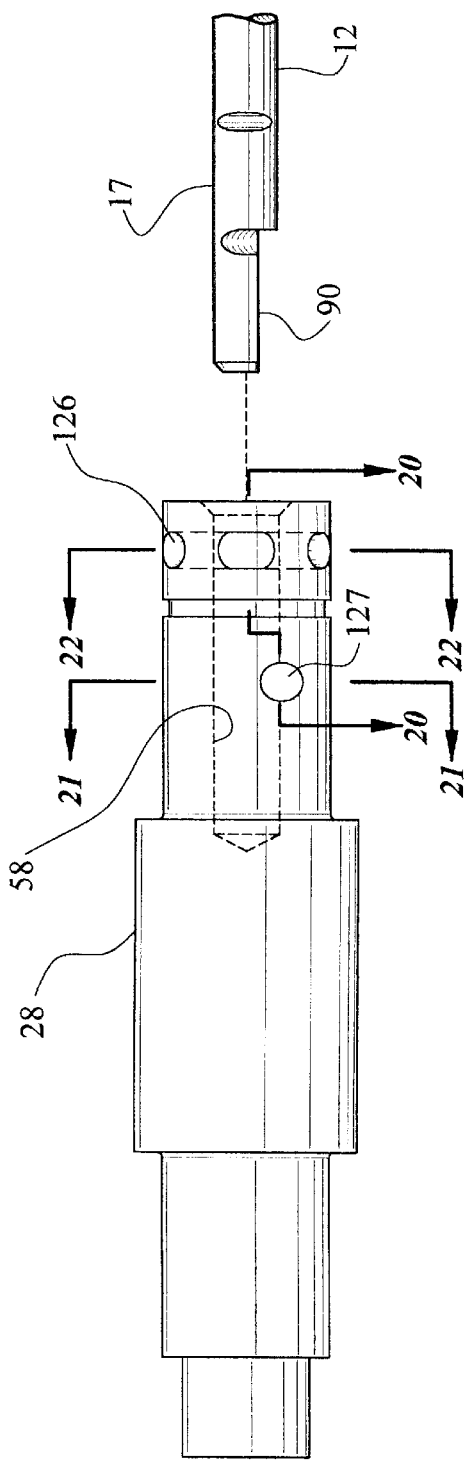
*FIG. 19*
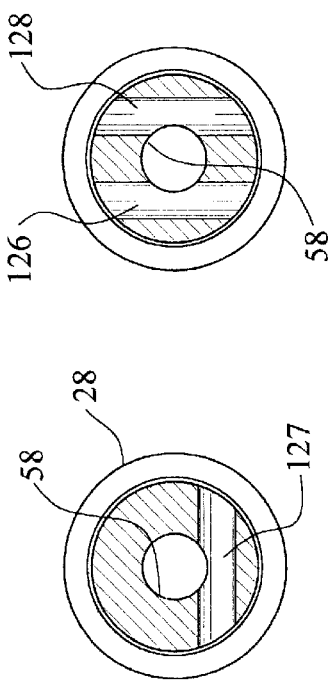
*FIG. 21*
*FIG. 22*
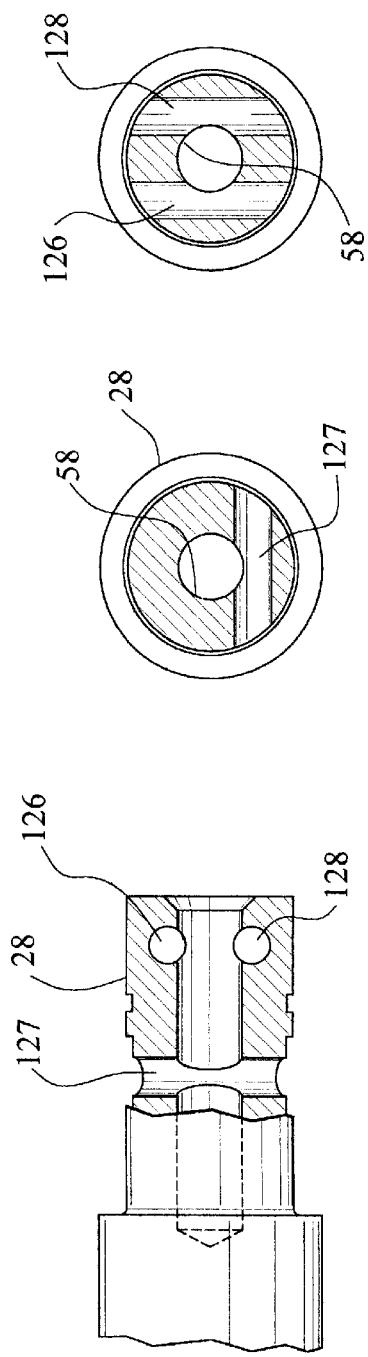
*FIG. 20*

HIGH SPEED SURGICAL INSTRUMENT

TECHNICAL FIELD

This invention relates to high speed surgical instruments and particularly to mechanism for providing a high speed drill having clutching mechanism for holding and locking cutters or tool bits into the surgical drill or attachment used for surgical procedures, with the feature of reducing the diameter of the cutting end to provide visualization to the user and to the combination of clutch mechanism and a unique designed cutter end for coupling the cutters tool bit to the surgical drill and/or attachment in the absence of mechanical moving parts. The surgical instrument includes unique bearings for supporting a cutter driven by a high speed drill, the cutter includes judicious cut out portions at the proximal end that cooperates with the clutch mechanism in the drill or in an attachment which may be bent and driven by the drill motor with the benefit that the diameter of the distal end of the attachment is made smaller than the diameter of the distal end of heretofore known surgical instruments.

CROSS REFERENCES

The following patent applications, contemporaneously filed with this patent application and assigned to the same assignee, relate to the subject matter of this patent application and are incorporated herein by reference. They include the patent application entitled "Bearings for Surgical Instruments" filed by Eddy H. Del Rio, Douglas A. Perry, Jose M. Lamanna, and Thomas D. Anspach, U.S. patent application Ser. No. 09/962,989 and the patent application entitled "Miniature Cutter Shaft Configuration" filed by Eddy H. Del Rio, Douglas A. Perry, Jose M. Lamanna and Thomas D. Anspach, U.S. patent application Ser. No. 09/962,461, now issued as U.S. Pat. No. No. 6,607,533.

BACKGROUND OF THE INVENTION

The surgical drill typically accommodates sundry tool bits such as cutting burrs, saw blades, etc, (cutters) and different sizes thereof and during a surgical procedure different tool bits and sizes may be required for use with the surgical drill. It is therefore necessary for the surgical drill or attachment sometimes referred to as a Micro Dissection Attachment (MDA) to provide means for coupling the tool bit easily and timely with a minimum of time required to remove the incumbent tool bit and replace it with a new one.

This invention constitutes an improvement on surgical drills and/or attachments by incorporating a unique design within the drill and/or attachment so as to be capable of easily locking the cutter in place. This invention is characterized as simple to assemble and disassemble, requiring minimum amount of time for performing these function, while having the ability to reliably secure or lock the cutter in the clutch mechanism. In accordance with this invention the tool bit is inserted in the surgical drill or attachment to a point beyond where the operator feels a slight force exerted by a latching spring and slightly rotates the tool bit to its locked position. The operator, of course, has no limitations as to when the rotation of the tool bit starts when inserted into the attachment and/or drill, except at the end of the travel. The removal is merely by turning and pulling on the tool bit simultaneously in the direction for removal from the drill or attachment. We have found that the assembly and disassembly, with a minimum of experimental time or leaning time to obtain the requisite skill, the procedure is almost instantaneous. The rotating mechanism of the drill and/or attachment needs to be held stationary during this procedure. Obviously, as is apparent from the above paragraphs, the clutch mechanism does not require movable parts as is typically utilized on drills that lock the tool bit into place.

U.S. Pat. No. 5,405,348 granted on Apr. 11, 1995 to William E. Anspach, Jr. and Eddy H. Del Rio, the joint inventor of the present application, and entitled "Surgical Cutting Instrument" exemplifies the cutters to which this invention pertains. In this patent it will be appreciated that the proximate end of the cutter fits into jaws of a clutch that is activated mechanically by positioning the jaws radially inward to bear against the outer surface of the cutter shaft to secure it in place during the drilling procedure and the jaws are retracted to release the cutter. Obviously, in the heretofore known mechanism of the type known and that being described herein, this procedure or similar procedure for assembly and disassembly of the cutter is not only cumbersome but is also time consuming. This invention constitutes an improvement of this type of mechanism by incorporating within the drill and/or attachment a unique attachment design for automatically retaining and locking the drill bit or cutter and which clutch mechanism is characterized by avoiding the typical manually operated clutching mechanism.

The invention is best described as having a combination of features that reduces the diameter of the support for the cutter to improve visibility for the surgeon, permits easy assembly and disassembly of the cutter or tool bit in a efficacious high speed surgical drill.

SUMMARY OF THE INVENTION

An object of this invention is to provide an improved clutch design for surgical drill and/or attachments wherein the proximal end of the cutter is configured to be easily assembled and disassembled in the unique designed automatic clutch mechanism.

A feature of this invention is that the clutch mechanism includes a hair pin shaped spring extending transversely through the wall of a rotating spindle or shaft of the drill and/or attachment to bear against the proximal end of the shaft of the cutter so as to bias the spindle or drill shaft to lock the cutter against a lock pin that also extends laterally into the bore of the spindle or drill shaft.

A clutch mechanism for a surgical drill or attachment that is characterized as relatively simple to fabricate, relatively inexpensive, easy to install the cutter into the clutch mechanism and to remove therefrom, is reliable to rotate with the drill motor and is rotatable in a clockwise and/or counterclockwise direction, and requires no mechanically moving jaws that are typically used with locking clutches.

A feature of this invention is an improved clutching mechanism in combination with a cutter with the cutter having a unique slot and groove configuration that mates with a generally U-shaped hair spring and pin for facilitating the assembly and disassembly of the cutter while locking the same and permitting clockwise and/or counterclockwise rotation.

Another feature is an improved attachment for a high speed surgical drill including a unique clutch in the attachment mating with a judicious groove arrangement formed on the proximal end of the cutter and for being supported in a reduced diameter tube attached to the attachment which reduction in diameter is a result of a unique bearing. The bearing is made from a polyimide resin/graphite compound that is formed in a journal bearing with a polygon shaped straight through central bore. The square bore configuration in a journal bearing made from a polyamide/graphite (60/40 ratio) resulted in a 3 mm diameter tube at the distal end, providing an efficacious surgical cutter instrument permitting the surgeon a line-on-line vision of the cutter at the cutting cite.

The foregoing and other features of the present invention will become more apparent from the following description and accompanying drawings.

BRIEF DESCRIPTION OF THE DRAWINGS

FIG. 12 is an exploded partial view in perspective showing the details of the clutch mechanism of this invention;

FIG. 13 is a perspective view of the spring used in the clutch mechanism of FIG. 12;

FIG. 14 is a perspective view taken from the top view of the spring depicted in FIG. 13;

FIG. 19 is a plan exploded view illustrating the position of the grooves and apertures formed in the cutter and clutch mechanism of this invention;

FIG. 20 is a fragmentary view partially in section of the spindle housing the clutch mechanism taken along lines 20—20 of FIG. 19;

FIG. 21 is a sectional view taken along the lines 21—21 of FIG. 19;

FIG. 22 is a sectional view taken along the lines 22—22 of FIG. 19;

These figures merely serve to further clarify and illustrate the present invention and are not intended to limit the scope thereof.

DETAILED DESCRIPTION OF THE INVENTION

Figure 1:
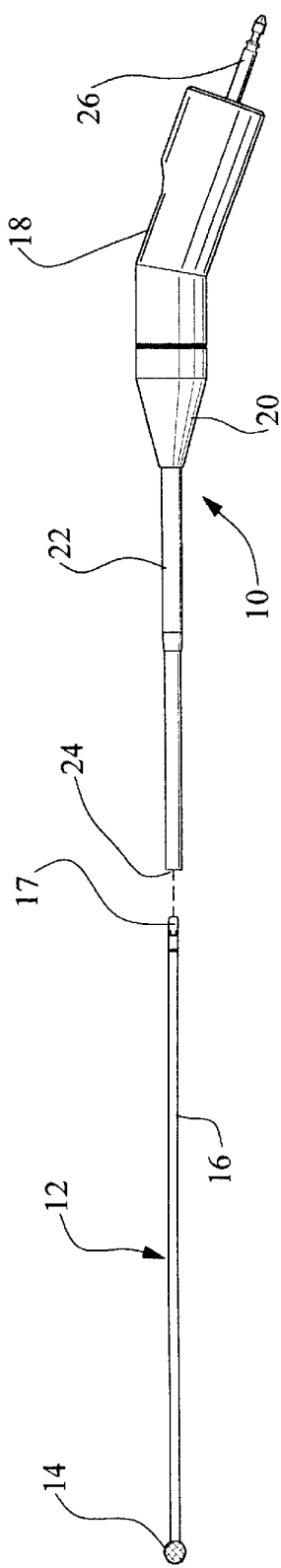
FIG. 1 is an exploded view in elevation illustrating the attachment for a surgical drill motor and the cutter of this invention.

To best understand this invention reference is made to FIG. 1 which discloses a MDA generally illustrated by reference numeral 10 which is dimensioned with a minimum diameter of 3 mm at the distal end, being 15 cm long and bent at a 20 degree (°) angle, for example, that rotatably supports a tool bit 12 or cutter having a cutting end 14 at the distal end, an elongated shaft 16 and a clutch portion 17 at the proximal end. The body of the MDA includes the angled housing 18, the nose cone member 20 extending from the fore end of the angled housing 18, an elongated tube assembly 22, that may be stepped toward the distal end 24 and the drive shaft 26 with its clutch shaped end that fits into the drill motor (not shown). The drill motor may be any of the surgical motors manufactured by the assignee of the present invention known in the industry as eMaX™ and microMax™or any other drill motor. (A suitable motor is commercially available from Anspach Companies, Palm Beach Gardens, Fla.). For additional information regarding surgical drills of the type being described herein reference should be made to U.S. Pat. Nos. 5,405,348, 5,494,359 and 5,601,560, which are incorporated herein by reference.

Figure 3:
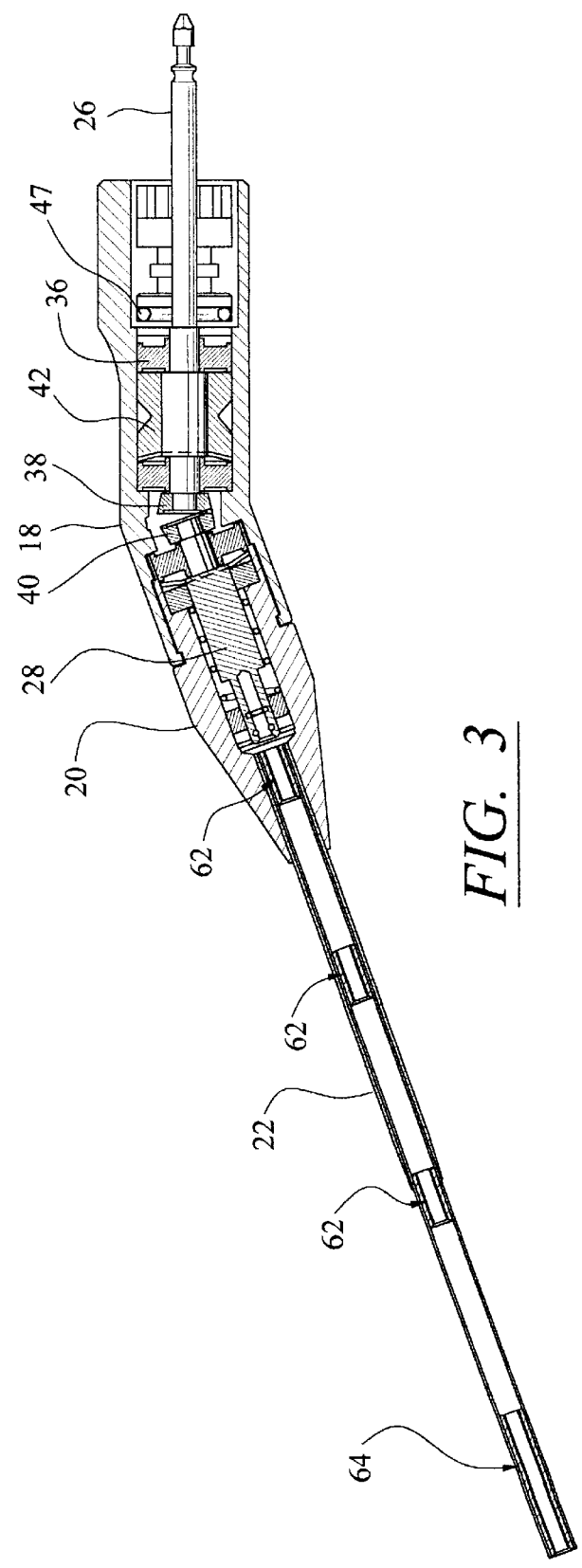
FIG. 3 is a sectional view of the assembled attachment depicted in FIG. 2.
Figure 2:
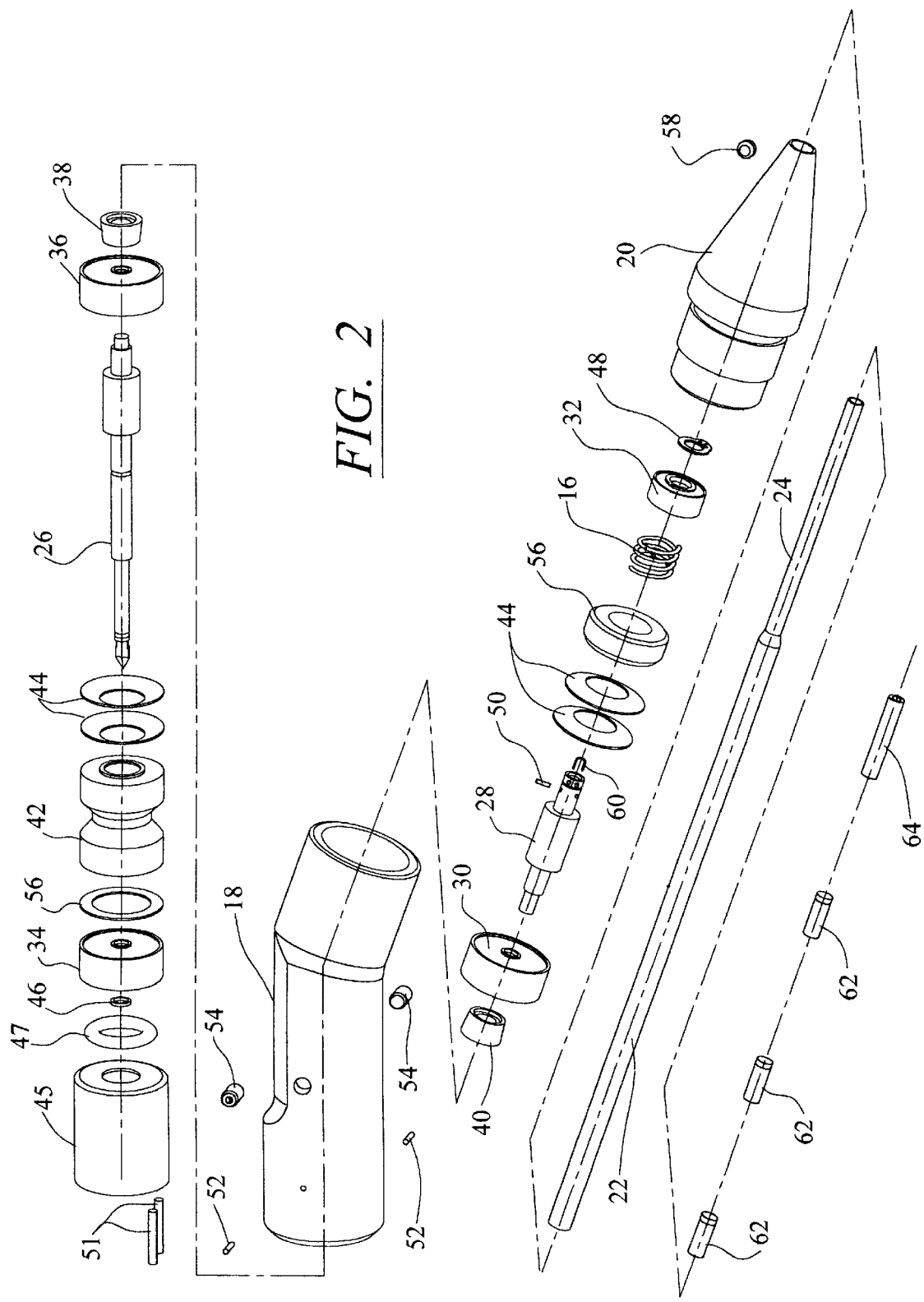
FIG. 2 is an exploded view in perspective of the details of the attachment depicted in FIG. 1.
Figure 4:
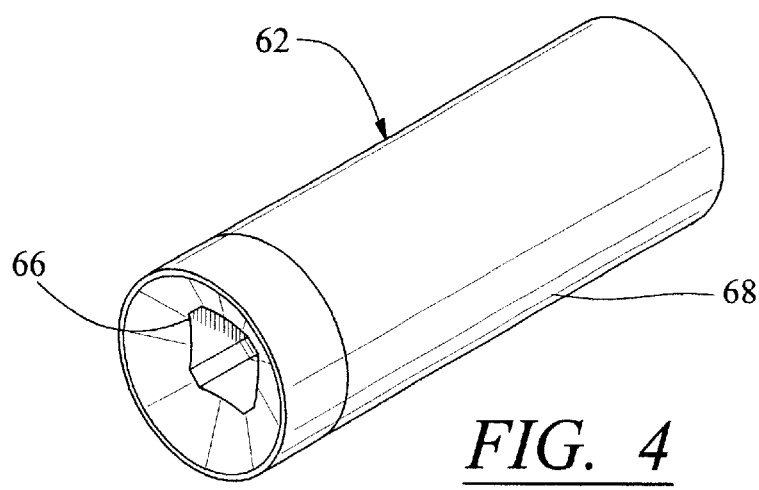
FIG. 4 is a perspective view of a bearing forming a portion of an embodiment of this invention.
Figure 5:
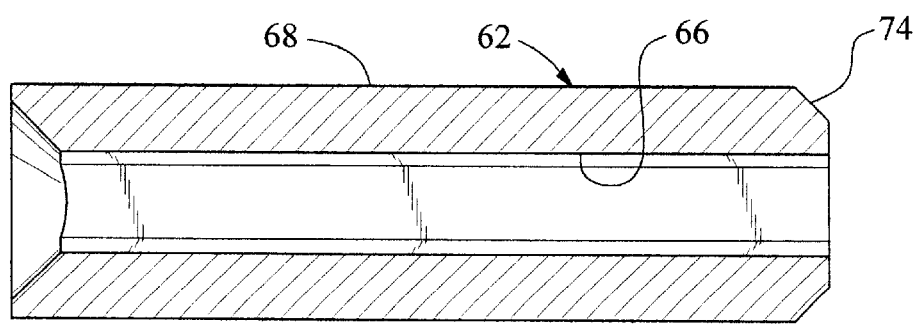
FIG. 5 is a sectional view of the bearing depicted in FIG. 4.
Figure 6:
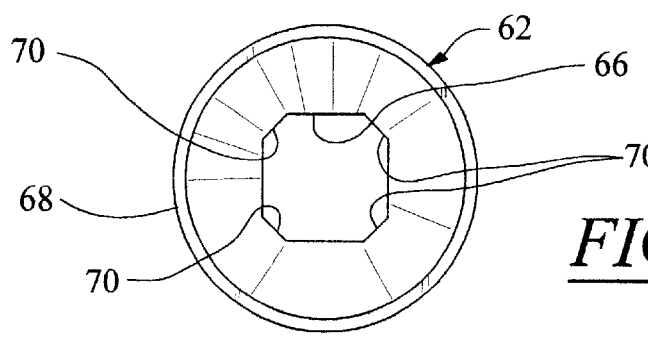
FIG. 6 is a front end view of the bearing depicted in FIG. 5.
Figure 7:
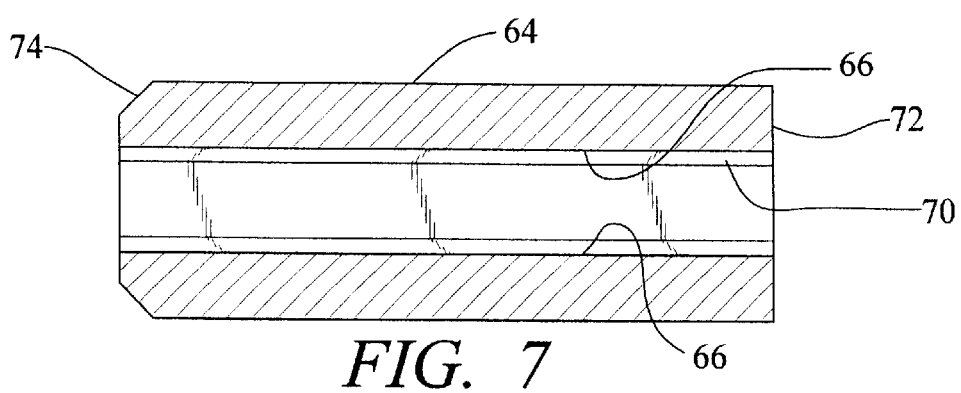
FIG. 7 is an enlarged and exaggerated schematic illustration of the square configuration and the two point contact of the bearing.
Figure 8:
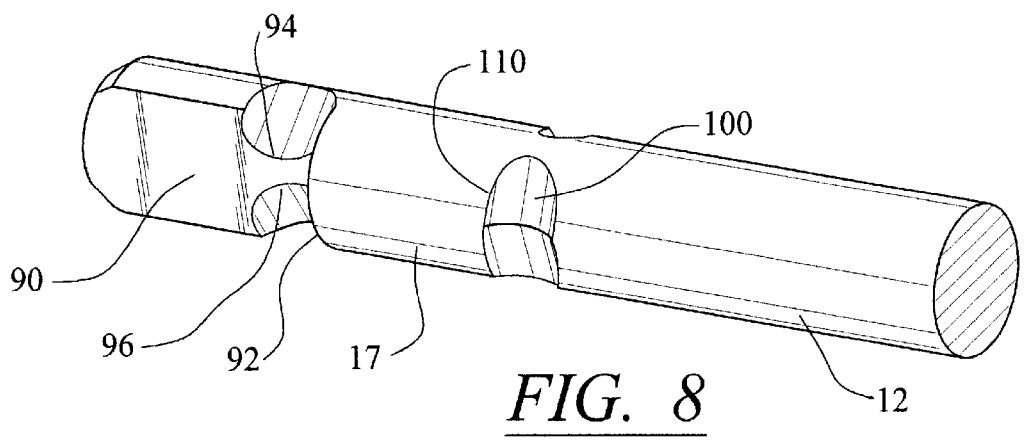
FIG. 8 is a fragmentary perspective view of the proximate end of the cutter.
Figure 9:
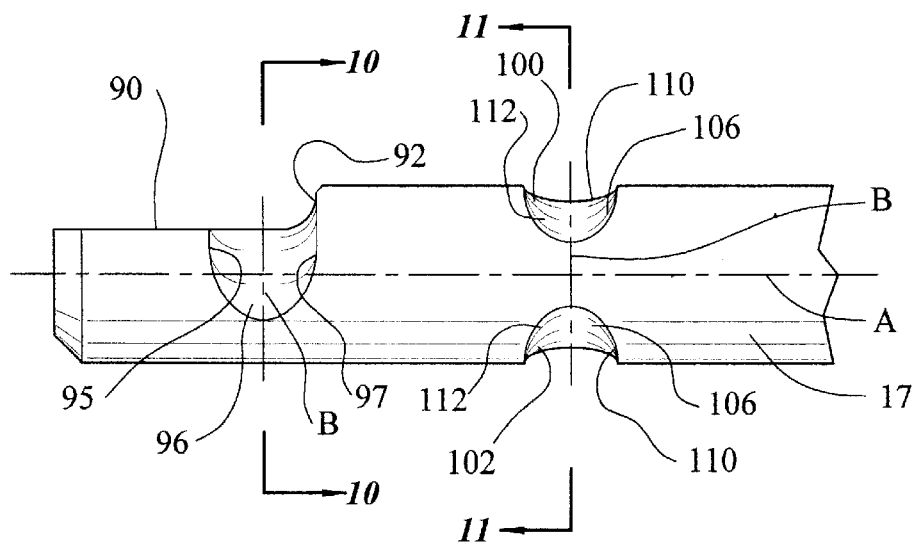
FIG. 9 is a fragmentary view in elevation of the proximal end of the cutter depicted in FIG. 8.
Figure 10:
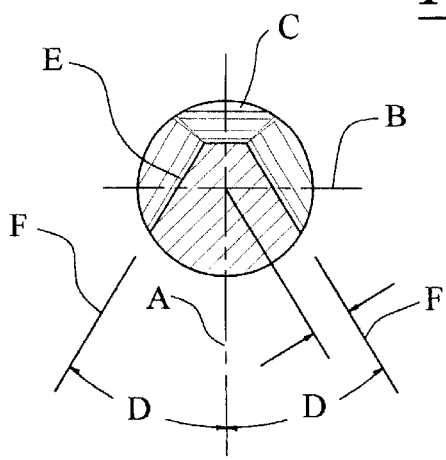
FIG. 10 is a sectional view taken from line 10—10 of FIG. 9.
Figure 11:
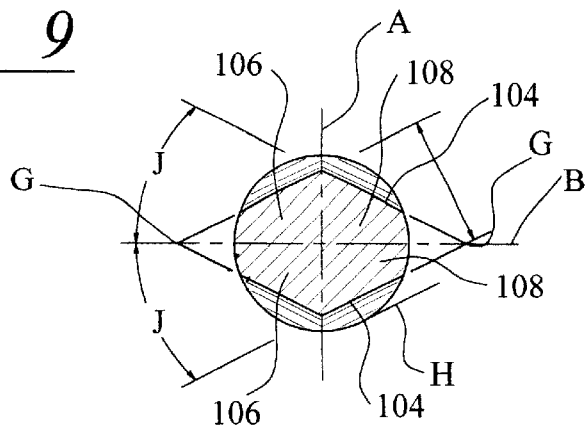
FIG. 11 is a sectional view taken from line 11—11 of FIG. 9.

Next referring to FIGS. 2 and 3 which illustrate the details of the MDA and the bearings of this invention which consists of a spindle 28 that is suitably rotatably supported by commercially available and suitable ball bearings 30 and 32. As is apparent from FIG. 3 the drive shaft 26 is also suitably rotatably supported in the angled housing 18 by commercially available and suitable ball bearings 34 and 36. As mentioned in the above paragraphs the drive shaft is suitably coupled to the drill motor (not shown) and driven thereby. The drill motor may use any medium for developing rotational movement and in this instance these motors are electrical. As noted, the spindle 28 is angled relative to the drive shaft 26 requiring beveled gears to change the relative angle. Suitable bevel gears 38 and 40 mounted on drive shaft 26 and spindle 28, respectively, provide this function. The thrust is absorbed by the thrust bearing 36 and the bearings are pre-loaded by the wave washer 57 and coil spring 16. The bushing 45 mounted in the aft end of the angle housing 18 is designed to accommodate the fitting connection in the drill motor which includes coupling mechanism that removably affix the MDA thereto. Suitable snap rings 46, 48, anti-rotation pins 51, spring pins 52 and set screws 54 are utilized to lock the respective components in the housing and together with the thrust washers 56 and wave washer 57 assure that the spindle is snugly fitted into the angled housing 18 and rotates efficaciously and attains long life. A seal 47 may be mounted in the angled housing at the drill attachment end to prevent contaminants from migrating internally and a suitable seal may be a commercially available "O" seal made from an elastomeric material. As mentioned in the above paragraphs, the drive motor and the MDA are merely used herein to describe the preferred embodiment. These bearings that are inserted into the tube assembly 22 which is affixed to the nose cone 20 by the set screw 58 and is held in a non-rotational position and serve to reduce the outer diameter of the distal end of the MDA.

The end of the shaft 16 of the drill bit 12 is configured to fit into a complementary configured retaining bore 58 formed internally of one end of the spindle 28 and together with the latch spring 60 and lock pin 50, locks the drill bit into place so that it rotates therewith and will be described in detail hereinbelow.

In this particular embodiment, four (4) similar bearings are utilized with the internal bearings generally indicated by reference numeral 62 and the distal end bearing generally indicated by reference numeral 64. For the sake of convenience and simplicity, only one of the internal bearings 62 and the distal end bearing 64 will be described.

All the bearings are made from a synthetic material and preferably polyimide resin and carbon or graphite. The best results have been obtained when the polyimide resin by volume equaled 60 percent (%) of the total volume and the carbon/graphite equaled 40% of the total volume. The material is obtained commercially and is made by Dupont under the trademark of "VESPEL". "VESPEL" SP-22 and SP-21 have been used and worked satisfactory. The intermediate bearing 62 are formed similar to a journal bearing with the inner straight through bore 66 formed in the cylindrical housing 68 is configured in a square shape in cross section and the corners 70 extending straight through the bore are beveled. The beveled portions are only incorporated to add material to the bearing, and hence, increase its structural integrity. The inlet portion, i.e. the portion facing the distal end 24 of the tube 22, is beveled in a countersunk manner so as to form a ramp to assist the end of the shaft 16 of the tool bit 12 to enter and pass into and/or through the bearing. The end portion 72 of bearing 64 at the distal end is squared off and hence, not countersunk. The proximal ends of the bearings 62 and 64 may be beveled in order to ease the assembly of the bearings when inserted into the tube 22. Obviously, the bearing outer diameter is selected to assure a tight fit with the interior surface of the tube 22.

The mating end of the cutter 12 is best understood by referring to FIGS. 8, 9, 10 and 11 which show the cutter 12 having a cut-out section at the proximal end 17 which is designed to be coupled to a clutch mechanism carried by the surgical drill motor assembly or in an attachment. The cutter is typically attached to the surgical drill motor to meet certain specifications for performing surgical procedures, as for example, transoral, transphernoidal and similar restricted access approaches. As mentioned in the hereinabove paragraphs, the cutters utilized with these types of bits are well known and the description to follow will focus on the proximate end that is uniquely designed for automatic clutching to be retained in the surgical drill or its attachment.

The end of the proximal end portion 17 is milled or flattened to form a planar portion 90 extending partly axially inward toward the distal end to define the shoulder 92. Adjacent to the shoulder 92 and in the planar portion 90 are a pair of diametrically opposed grooves 94 and 96 cut into the shaft 12 and each defining a truncated triangle E with the removed extended apex C (see FIG. 10) forming angle D substantially equal to a 30 degree (°) angle with respect to a plane A extending centrally of the transverse (vertical) axis bisecting the plane B extending centrally of the axial (horizontal) axis and perpendicular therewith. It will be appreciated from FIG. 10 that the apex C lies in coincidence with the top surface of the planar portion 90. Hence, the groove begins from the flat and has a front wall 95 toward the proximal end 17 of the shaft 12 and a rear wall 97 toward the distal end 14 of shaft 12.

Spaced a short axial distance from shoulder 92 and toward the distal end 14 of shaft 12, are a pair of groove configurations 100 and 102 diametrically opposed to each other and each groove configurations 100 and 102 includes a groove 104 having an extended apex G (see FIG. 11) lying in coincidence with the plane B and a diametrically opposed groove 106 lying in coincidence with plane B and also having an extended apex G each defining a triangle with an angle J being substantially equal to 25°. As will be noted from FIG. 9 the grooves 106 and 108 start just below the outer circumference of the shaft 12, say at substantially 0.010 inch and the intersection of the base H which is in coincidence with the plane A. As is apparent from the foregoing the groove configurations 100 and 102 are configured identical to each other and when installed in the clutch mechanism of the surgical drill or its attachment, the groove configurations allow the drill bit to be rotated either clockwise or counterclockwise directions. Each of the grooves 106 and 108 have a back wall 110 facing the proximate end 14 of shaft 12 and a forward wall 112 facing the distal end 17 of shaft 12. The back wall 97 and the back wall 110 are parallel to each other.

Figure 16:
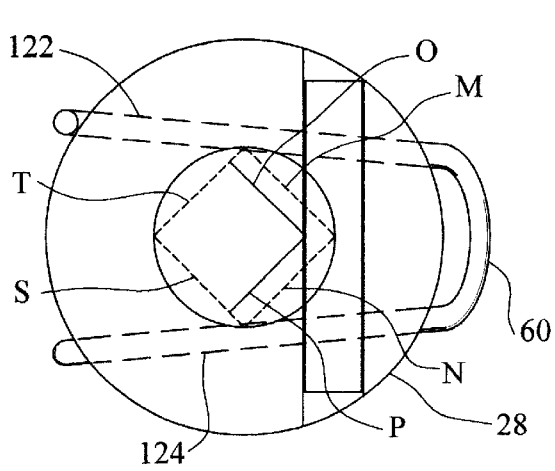
FIG. 16 is a schematic view illustrating the relationship of the cutter and the clutch mechanism of this invention in the orientation depicted in FIG. 15.
Figure 18:
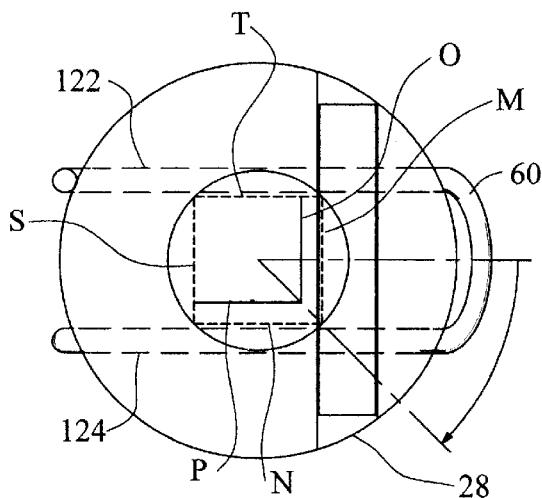
FIG. 18 is a schematic view illustrating the relationship of the cutter and the clutch mechanism of this invention in the orientation depicted in FIG. 17.
Figure 15:
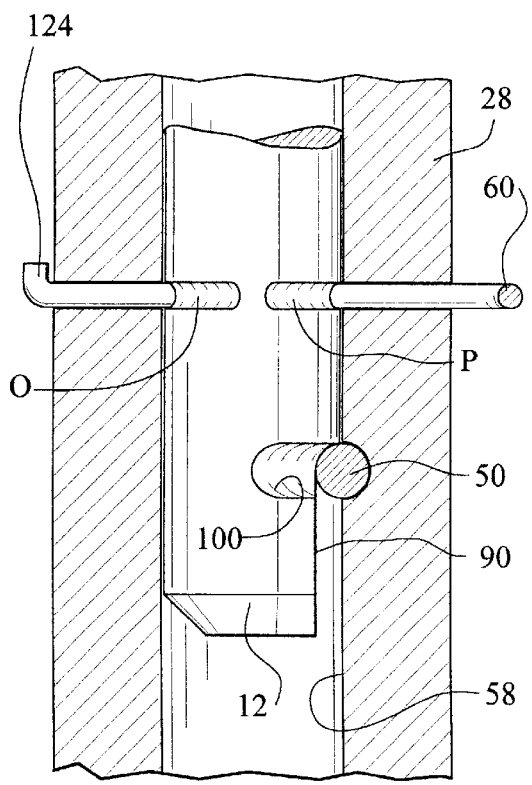
FIG. 15 is a fragmentary view in section illustrating the insertion of the cutter into the clutch mechanism of this invention.
Figure 17:
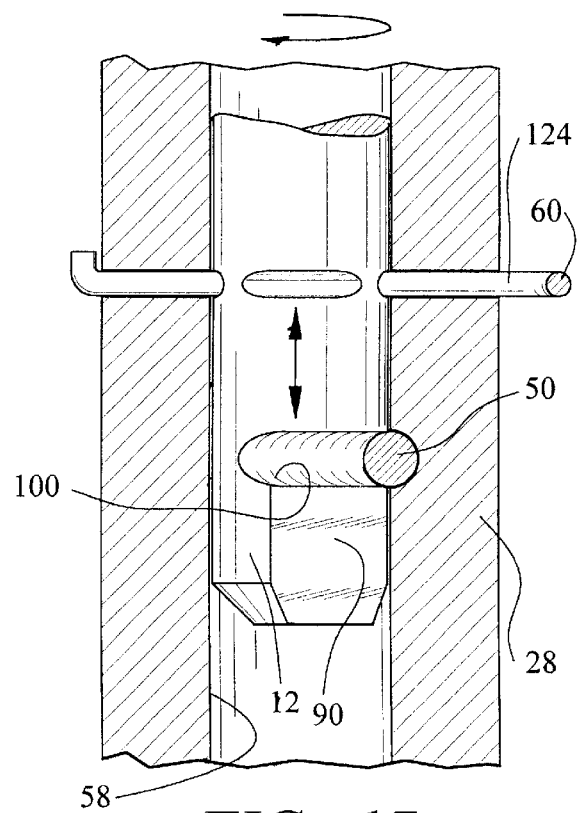
FIG. 17 is a fragmentary view similar to the mechanism depicted in FIG. 15 illustrating the cutter when it is in the retained and locked position.

The next portion of this description will describe the clutch which may be formed in either the MDA or surgical drill and for description purposes only, the clutch will be described in connection with the MDA and as one skilled in this art will appreciate, the clutch can be mounted in the drill itself. As noted in FIG. 2, the clutch is mounted in the spindle 28 which is best shown in FIGS. 2 and 12–22 comprising the U-shaped spring 60 and the pin 50 where the pin 50 which traverses through the bore 58 formed in spindle 28 and is judiciously located. As noted from FIGS. 15 and 17 the pin 50 fits into drilled hole 157 (see FIG. 12) that laterally extends through the spindle 28 and intersecting bore 58 similarly to the spring 60 and suitably secured to spindle 28 by any well known means. In this instance the pin 50 is retained in spindle 28 by the race of bearing 32. The spring 60 is slightly distorted so that the legs 122 and 124 are out of plane with each other. The spring 60 is mounted in the laterally spaced holes 126 and 128 that extend therethrough and bisect the bore 58 and are judiciously located so that when the proximate end of the cutter 12 is inserted it will extend pass the legs 122 and 124 and will be sandwiched there between. The ends 130 and 132 of legs 122 and 124 are bent to say 90° to hold the spring into place and the legs bear against the walls of the holes 126 and 128 to bias the spindle 26 so that it will rotate slightly to align the pin 50 with respect to the shoulder 92 of groove 90 which is best depicted in FIGS. 16–18. As can be seen in FIG. 15, when the cutter 12 is inserted so that the end portion 17 and the flat portion 90 pass the spring 60 the shoulder 92 will bear up against the pin 50. As mentioned earlier, the combined effect of the user rotating the cutter as it is inserted and the biasing effect of spring 60 on spindle 28 causes the cutter 12 to rotate and spindle 28 will be rotated so that the shoulder 95 bears against the pin 50 and prevents the cutter from dislodging from its position. It will also be appreciated from FIGS. 16 and 18 the configuration M, N, O, P, S, T. of the shoulders and grooves 94, 96 and 100, 102 are selected to define a locking support that prevents the cutter not only from being dislodged but also prevents any backlash so that the surgeon will have the confidence that the cutter will follow his motions. Obviously, removing the cutter from the clutch, merely requires the operator holding the shaft from rotating which can easily be done by holding the end of spindle 26, and retracting the cutter as it is being rotated slightly and the groove 100 will be slightly rotated and expose the pin 50 to the space provided by the flat portion 90 and the wall surface of the bore 58 in spindle 28 permitting the cutter to pass the pin and sliding out of the MDA.

FIGS. 19–22 are included herein to illustrate the relationship of the spring 60 and pin 50 and the apertures formed in spindle 28. As is apparent from these Figs. The drilled holes 126 and 128 are diametrically opposed to each other and are dimensioned to allow the spring 60 to pass therebetween when assembled. Obviously, each hole 126 and 128 bisect the bore 58 so that each leg of spring 60 contacts the cutter outer surface. The drilled hole 127 that extends laterally through the spindle 24, likewise bisects the bore 58 so that the proximal end of the cutter will pass the pin 50. Obviously, the flat portion 90 will provide the widest gap with the wall of bore 58 when the cutter is allowed to pass by the pin 50. Rotation of the cutter and/or spindle 28 will re-position the flat portion 90 and the cutter is now in the trapped position in either groove 94 or 96 depending on the rotation of the drill, i.e. either clockwise or counter clockwise.

Although this invention has been shown and described with respect to detailed embodiments thereof, it will be appreciated and understood by those skilled in the art that various changes in form and detail thereof may be made without departing from the spirit and scope of the claimed invention.

We claim:

1. A clutch for a high speed drill supporting a cutter for surgical use and said high speed drill including a rotating spindle having a bore at one end, said rotating spindle having a lateral opening and another lateral opening circumferentially spaced from said lateral opening, said clutch including a U-shaped spring having a first leg extending through said lateral opening in said rotating spindle and intersecting said bore and a second leg extending through said another lateral opening radially spaced from said lateral opening and also intersecting said bore and defining between said first leg and said second leg a spaced passageway, a pin extending laterally through an aperture in said spindle and intersecting said bore, said pin being axially spaced from said U-shaped spring whereby said U-shaped spring and said pin accommodate a predetermined configuration in the cutter for automatically locking the cutter into the high speed drill.

2. A clutch for a high speed drill supporting a cutter for surgical use as claimed in claim 1 wherein said U-shaped spring includes a bent end portion on both the said first leg and the said second leg and both end portions located externally of said rotating spindle in the assembled condition for securing said spring to said rotating spindle.

3. A clutch for a high speed drill supporting a cutter for surgical use as claimed in claim 2 wherein said first lateral opening and said second lateral opening includes a wall surface, said first leg is distorted so as to lie in a different plane from said another second leg wherein and said first leg and said second leg bear against said wall surface to bias said spindle in a rotary direction.

4. A clutch for an adapter attached to a high speed drill supporting a cutter for surgical use, said adapter including a rotating spindle having a bore at one end, said rotating spindle having a lateral opening and another lateral opening circumferentially spaced from said lateral opening, said clutch including a U-shaped spring having a first leg extending through said lateral opening in said rotating spindle and intersecting said bore and a second leg extending through said another lateral opening radially spaced from said lateral opening and also intersecting said bore and defining between said first leg and said second leg a spaced passageway, a pin extending laterally through an aperture in said spindle and intersecting said bore, said pin being axially spaced from said U-shaped spring whereby said U-shaped spring and said pin accommodate a predetermined configuration in the cutter whose proximal end passes through said passageway and bears against said pin for automatically locking the cutter into said adapter.

5. A clutch for an adapter attached to a high speed drill supporting a cutter for surgical use as claimed in claim 4 wherein said U-shaped spring includes a bent end portion on both said first leg and said second leg and said bent ends being located externally of said rotating spindle in the assembled condition for securing said spring to said rotating spindle.

6. A clutch for an adapter attached to a high speed drill supporting a cutter for surgical use as claimed in claim 5 wherein said first lateral opening and said another second lateral opening includes a wall surface, said first leg is distorted so as to lie in a different plane relative to with said second leg and said first leg and said second leg bear against said wall surface to bias said spindle in a rotary direction.

7. In combination, a clutch for high speed drill and a cutter supported thereby for surgical use, said said high speed drill including a rotating spindle having a bore at one end, said rotating spindle having a lateral opening and another lateral opening circumferentially spaced from said lateral opening, said clutch including a U-shaped spring having a first leg extending through said lateral opening in said rotating spindle and intersecting said bore and a second leg extending through said another lateral opening radially spaced from said lateral opening and also intersecting said bore and defining between said first leg and said second leg a spaced passageway, a pin extending laterally through an aperture in said spindle and intersecting said bore, said pin being axially spaced from said U-shaped spring, said cutter having a proximate end and a distal end, said cutter having a shank portion, a cutting surface at the distal end, and a cut-out configuration portion adapted to be locked by said clutch, said cutter being circular in cross section, a milled out portion defining a flat surface formed on the distal end extending a short distance toward the proximate end, a first pair of opposing radially extending grooves adjacent to said flat portion and a second pair of radially extending grooves axially spaced from said first pair of radially extending grooves and said pin accommodate a predetermined configuration in the cutter for automatically locking the cutter into said clutch of the high speed drill.

8. The combination as claimed in claim 7 wherein said U-shaped spring includes a bent end portion on said first leg and another bent end portion on said second leg, said bent end portion and said another bent end portion located externally of said rotating spindle in the assembled condition for securing said spring to said rotating spindle.

9. The combination as claimed in claim 8 wherein said first lateral opening and said second lateral opening includes a wall surface, said first leg is distorted so as to lie out of the plane of with said second leg and said first leg and said second leg bear against said wall surface to bias said spindle in a rotary direction.

10. The combination as claimed in claim 9 including a shoulder formed adjacent to the end portion of said flat portion remote from said proximate end.

11. The combination as claimed in claim 10 wherein said first pair of radially extending grooves including one of said pair of radially extending grooves having a groove dimension that forms substantially a 30 degree angle relative to a plane extending transversely through the center of said shank and the other of groove of said pair of grooves having a groove dimension that forms substantially a 30 degree angle relative to a plane extending transversely through the center of said shank and each of said grooves of said pair of radially extending grooves being on opposite sides of said shank and having a common apex.

12. The combination as claimed in claim 11 wherein said second pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

13. The combination as claimed in claim 12 wherein said apex of said second pair of grooves is below the outer source of said shank.

14. The combination as claimed in claim 13 wherein said shank includes a third pair of grooves diametrically opposed to said second pair of grooves.

15. The combination as claimed in claim 14 wherein said third pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

16. The combination as claimed in claim 15 wherein said apex of said second pair of grooves is below the outer surface of said shank.

17. In combination, a clutch for high speed drill and bearing for supporting a cutter in the high speed drill for surgical use, said said high speed drill including a housing and a rotating spindle, said rotating spindle having a bore at one end, said clutch including a U-shaped spring having a first leg extending through a lateral opening in said rotating spindle and intersecting said bore and a second leg extending through another lateral opening radially spaced from said lateral opening and also intersecting said bore and defining between said first leg and said second leg a spaced passageway, a pin extending laterally through an aperture in said spindle and intersecting said bore, said pin being axially spaced from said U-shaped spring, said bearing being supported in a housing, said high speed rotating shaft mounted in said straight through bore, said straight through bore of said bearing having four side wall surfaces defining in cross section a substantially square shape, the dimensions of the diameter of said high speed rotating shaft and the area of the cross section of said straight through bore being selected so that said high speed rotating shaft bears at point contact against two side wall surfaces of said four side wall surfaces and said bearing being made from material taken from the group consisting essentially of polyimide resin and graphite.

18. The combination as claimed in claim 17 wherein the volume of the polyimide is substantially equal to between 60%–85% of the total volume and the volume of graphite is substantially equal to between 40%–15% of the total volume of the material.

19. The combination as claimed in claim 17 wherein the volume of the polyimide is substantially equal to 60% of the total volume and the volume of graphite is substantially equal to 40% of the total volume of the material.

20. The combination as claimed in claim 17 wherein the four side surfaces define four corners of the straight through bore and each of said corners being faired to define an extended surface to increase the total amount of material forming said bearing so as to increase the structural integrity of the bearing.

21. The combination as claimed in claim 18 wherein said bearing includes a fore end and an aft end, said fore end being countersunk to define a ramp for guiding said high speed rotating shaft into said bearing when installing said high speed rotating shaft.

22. In combination, a clutch for high speed drill, and bearing supporting the cutter in the housing of said high speed drill for surgical use, said high speed drill including a rotating spindle having a bore at one end, said rotating spindle having a lateral opening and another lateral opening circumferentially spaced from said lateral opening, said clutch including a U-shaped spring having a first leg extending through said opening in said lateral rotating spindle and intersecting said bore and a second leg extending through said another lateral opening radially spaced from said lateral opening and also intersecting said bore and defining between said first leg and said second leg a spaced passageway, a pin extending laterally through an aperture in said spindle and intersecting said bore, said pin being axially spaced from said U-shaped spring, said cutter having a proximate end and a distal end, said cutter having a shank portion, a cutting surface at the distal end, and a cut-out configuration portion adapted to be locked said clutch, said cutter being circular in cross section, a milled out portion defining a flat surface formed on the distal end extending a short distance toward the proximate end, a first pair of opposing radially extending grooves adjacent to said flat portion and a second pair of radially extending grooves axially spaced from said first pair of radially extending grooves and said pin accommodate a predetermined configuration in the cutter for automatically locking the cutter into said clutch of the high speed drill, said bearing being supported in said housing, said shank portion mounted in said straight through bore for high speed rotation, said straight through bore of said bearing having four side wall surfaces defining in cross section a substantially square shape, the dimensions of the diameter of said high speed rotating shank portion and the area of the cross section of said straight through bore being selected so that said high speed rotating shaft bears at point contact against two side wall surfaces of said four side wall surfaces and said bearing being made from material taken from the group consisting essentially of polymide resin and graphite.

23. The combination as claimed in claim 22 wherein said U-shaped spring includes a first bent end portion on said first leg and a second bent end portion on said second leg and said first bent end portion and said second bent end portion located externally of said rotating spindle in the assembled condition for securing said spring to said rotating spindle.

24. The combination as claimed in claim 23 wherein said first lateral opening and said second lateral opening includes a wall surface, said first leg is distorted so as to be in a different plane relative to with said second leg and said first leg and said second leg bear against said wall surface to bias said spindle in a rotary direction.

25. The combination as claimed in claim 24 including a shoulder formed adjacent to the end portion of said flat portion remote from said proximate end.

26. The combination as claimed in claim 25 wherein said first pair of radially extending grooves including one of said pair of radially extending grooves having a groove dimension that forms substantially a 30 degree angle relative to a plane extending transversely through the center of said shank and the other of groove of said pair of grooves having a groove dimension that forms substantially a 30 degree angle relative to a plane extending transversely through the center of said shank and each of said grooves of said pair of radially extending grooves being on opposite sides of said shank and having a common apex.

27. The combination as claimed in claim 26 wherein said second pair of radially extending grooves includes a first groove of said pair of radially extending grooves having a groove dimension that forms substantially a 25 degree angle relative to a plane extending transversely through the center of said shank and a second groove having a groove dimension that forms substantially a 25 degree angle relative to a plane extending transversely through the center of said shank and having an apex common to the apex of said first groove.

28. The combination as claimed in claim 27 wherein said apex of said second pair of grooves is below the outer surface of said shank.

29. The combination as claimed in claim 28 wherein the volume of the polyimide is substantially equal to between 60%–85% of the total volume and the volume of graphite is substantially equal to between 40%–15% of the total volume of the material.

30. The combination as claimed in claim 29 wherein the volume of the polyimide is substantially equal to 60% of the total volume and the volume of graphite is substantially equal to 40% of the total volume of the material.

31. The combination as claimed in claim 30 wherein the four side surfaces define four corners of the straight through bore and each of said corners being faired to define an extended surface to increase the total amount of material forming said bearing so as to increase the structural integrity of the bowing.

32. The combination as claimed in claim 31 wherein said bearing includes a fore end and an aft end, said fore end being countersunk to define a ramp for guiding said high speed rotating shaft into said bearing when installing said high speed rotating shank.

* * * * *